United States Patent [19]

Schwan et al.

[11] Patent Number: 5,424,062
[45] Date of Patent: Jun. 13, 1995

[54] METHOD FOR PERMANENTLY SHAPING HAIR

[75] Inventors: Annette Schwan, Darmstadt; Günther Lang, Reinheim; Thomas Clausen, Alsbach, all of Germany

[73] Assignee: Wella Aktiengesellschaft, Darmstadt, Germany

[21] Appl. No.: 134,172

[22] Filed: Oct. 8, 1993

Related U.S. Application Data

[63] Continuation of Ser. No. 806,882, Dec. 12, 1991, abandoned.

[30] Foreign Application Priority Data

Dec. 21, 1990 [DE] Germany .................. 40 41 164.8

[51] Int. Cl.⁶ .......................... A61K 7/09; A45D 7/04
[52] U.S. Cl. ................... 424/70.5; 424/70.4; 424/70.2; 132/204
[58] Field of Search ............. 424/71, 72, 70.5, 70.4, 424/70.2; 528/12, 342; 132/204

[56] References Cited

U.S. PATENT DOCUMENTS 3,981,312  9/1976  Patel ........................ 424/70
4,895,917  1/1990  Grüning .................... 528/10
5,071,641  12/1991 Lewis ....................... 424/71

FOREIGN PATENT DOCUMENTS 0346151  12/1989  European Pat. Off. .
1423342  2/1976  United Kingdom .

*Primary Examiner*—Thurman K. Page
*Assistant Examiner*—Sally Gardner
*Attorney, Agent, or Firm*—Michael J. Striker

[57] ABSTRACT

The process for permanent shaping of hair including the steps of treating the hair with a hair shaping agent, bringing the hair into a desired shape before and/or after treating the hair with the shaping agent, rinsing with water as needed, subjecting the hair to an oxidative aftertreatment, setting the hair to form a permanent wave and drying. To provide a permanent shaping which does not leave the hair with an unpleasant odor and is safe for the hair, the hair shaping agent consists essentially of an aqueous composition containing from 0.1 to 30% by weight of at least one Bunte-salt and from 0.5 to 30% by weight of at least one sulfite or hydrogen sulfite. The sulfites and hydrogen sulfites are selected from the group consisting of alkali metal and ammonium sulfites and hydrogen sulfites and alkanolamine salts of sulfurous acid. The Bunte-salts include various thiosulfate-containing compounds.

7 Claims, No Drawings

METHOD FOR PERMANENTLY SHAPING HAIR

This is a continuation of application Ser. No. 806,882, filed Dec. 12, 1991, now abandoned.

BACKGROUND OF THE INVENTION

The present invention relates to a process for permanently shaping hair.

The permanent shaping of hair occurs in a known method including the steps of first treating the hair with a keratin-reducing thiocompound, such as a mercaptocarboxylic acid or a mercaptocarboxylic ester, then shaping the hair into its new form and subsequently subjecting the hair to an oxidative aftertreatment with an oxidizing solution, i.e. "fixing" the hair.

Several disadvantages are connected with this prior art method. The hair frequently has an unpleasant mercaptan-like odor after treatment, which in a few cases is still present days after the permanent treatment. Furthermore allergic reactions can occur using mercaptocarboxylic esters, while hair damage cannot be completely prevented using mercaptocarboxylic acid salts because of their high pH.

It has already been proposed many times to use sulfite-containing agents instead of thiocontaining reducing agents for the treatment methods, since sulfite-containing shaping agents have advantages compared to thio-containing agents. Sulfite-containing shaping agents have no disturbing smell, are not sensitizing and complete their shaping action already in the neutral pH range, so that a hair shaping method which is safe for the hair and skin could be possible.

A disadvantage of hair shaping with sulfite-containing agents is however, that the hair keratin may be stabilized after the shaping step only with great difficulty (that means a restoration of the original state of the hair is not possible), since the oxidative aftertreatment usually used with thio-containing shaping agents results in inefficient stabilization and the stabilization by intense washing with water is not satisfactory.

For these reasons a hair-shaping based on sulfite-containing shaping agents has resulted in only a moderate permanance or stability. Also the hair so treated feels rough and variable.

In European Published Patent Application 0 346 151 it is thus suggested to use alkali preparations for hair shaping, which contain a Bunte-salt in addition to alkali or ammonium sulfite. These Bunte-salts should, before the stabilizing rinsing step with water, be thermally bonded to the hair while protecting the moist hair with a foil. Because of that an improvement of the permanance or stability of the shaped hair is obtained, since the Bunte-salt reacts with the thio-groups of the hair keratins and causes an increased cross-linking in the hair. An oxidative aftertreatment does not succeed.

This method has the disadvantage however that it is very time consuming, since every permanent wave curler must be curled in a separate foil so that a satisfactory wave results. The shaping process used in this process also has a very high pH-value (pH>10), whereby the hair is very strongly stressed. Because of the strong stressing of the hair keratin, the hair treated in this way has a poor feel and is difficult to arrange in the dry state.

SUMMARY OF THE INVENTION

It is an object of the present invention to provide a process for permanent shaping of hair, which allows a hair- and skin-saving shaping and guarantees a good stability of the shaped hair.

It is also an object of the present invention to provide a method of permanent shaping of hair, which provides permanently shaped hair free of undesirable odor, which has a good feel, while at the same time does not sensitize the hair and the skin.

These objects and others, which will be made more apparent hereinafter, are attained in a method of permanently shaping hair comprising treating the hair with a treatment agent before and/or after bringing the hair into the desired shape, rinsing as needed with water, then subjecting the hair to an oxidative aftertreatment, rinsing with water, if needed setting in a permanent wave and then drying.

According to the present invention, the method for permanently shaping hair includes using an aqueous preparation as shaping agent, which contains at least one sulfite or hydrogen sulfite as well as at least one Bunte-salt.

It has been surprisingly found that these objects can be attained by a method or process in which hair is shaped with a shaping agent which contains a sulfite or hydrogen sulfite as well as a Bunte-salt and is subsequently treated in an oxidative aftertreatment, in a particularly outstanding way.

In one embodiment of the method according to the invention the hair is first washed with a Shampoo and then rinsed with water. Subsequently the hand towel-dried hair is divided into separate strands and wound on curlers with a diameter of from about 5 to 15 millimeters, and a sufficient amount, advantageously about 80 to 120 grams, of the shaping agent for hair shaping is applied to the hair.

In another embodiment of the method of the invention the hand towel-dried hair is pre-moistened with a portion of the shaping agent, advantageously about 40 to 60 grams, divided into individual strands and wound on curlers. Then the residual shaping agent, advantageously about 40 to 60 grams, is applied to the hair.

The shaping agent used in the method described here is an aqueous preparation, which contains a mixture of one or more sulfites or hydrogen sulfites and one or more Bunte-salts.

The sulfite or hydrogen sulfite of the invention is advantageously an alkali metal sulfite or an alkali metal hydrogen sulfite, e.g. sodium sulfite or sodium hydrogen sulfite, ammonium sulfite or ammonium hydrogen sulfite and alkanolamine salts of sulfurous acid in an amount of 0.5 to 30 percent by weight, advantageously 2 to 12 percent by weight.

The following monomeric or polymeric Bunte-salts or mixtures of Bunte-salts, which include thiosulfate-containing compounds, can be used in the shaping agent of the process described here:

(i) 2-S-thiosulfatocarboxylic acids of the following general formula (I):

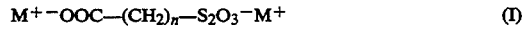

$$M^+{}^-OOC-(CH_2)_n-S_2O_3{}^-M^+ \qquad (I)$$

with n equal to a whole number from 1 to 6 and $M^+$ is an alkali metal or ammonium cation;

(ii) 2-S-thiosulfatoethylamine of the following general formula (II)

$$H_2N-CH_2-CH_2-S_2O_3^- M^+ \quad (II)$$

with $M^+$ = alkali metal or ammonium cation;
(iii) Polyamide-Epichlorohydrin- Bunte-Salt of the general formula (III)

$$P-N-CH_2-CH(OH)-CH_2-S_2O_3^- M^+ \quad (III)$$

with $M^+$ being an alkali metal- or ammonium cation and P = a polymer chain;
(iv) polyoxyalkylene-Bunte-salts of the general formula (IV) or (V)

$$[(O\text{-alkylene})_m OH]_q R[(O\text{-alkylene})_m O \, X \, S_2O_3 Y]_p \quad (IV)$$

$$Y \, O_3S_2 \, X-(O\text{-alkylene})_m-X \, S_2O_3 \, Y \quad (V),$$

wherein
p = 2, 3, 4, 5 or 6;
q = 0, 1, 2, 3 or 4;
(p+q) = 3, 4, 5 or 6;
m = a whole number > 1;
R is a group, which is obtained by cleavage of a hydroxyl group from an aliphatic alcohol with at least 2 carbon atoms;
X is a divalent substituted or unsubstituted aliphatic group with one to 10 carbon atoms; and
Y is a hydrogen atom, a salt-forming ion or a salt-forming group;
(v) (3-S-thiosulfato-2-hydroxypropyl)-N, N-dimethylamine of the following general formula (VI)

$$(CH_3)_2N-CH_2-CH(OH)-CH_2-S_2O_3 \quad (VI);$$

(vi) keratin-Bunte-salts obtained by reaction of keratin hydrolysates (e.g. kerasol$^R$ of Croda Ltd. Company, Great Britain) with sodium thiosulfate; and
(vii) polysiloxane- Bunte-salts of the general formula (VII):

$$R^1{}_a - \underset{\underset{R^2{}_b}{|}}{Si} - O_{[(4-a-b)/2]} \quad (VII)$$

wherein from 90 to 100% of the $R^1$ groups are methyl, and from 0 to 10% of the $R^1$ groups are phenyl;
and $R^2 = R^3$ and/or $R^4$,
wherein $$R^3 = -(C_nH_{2n})-O-(C_mH_{2m}O)_p-R^5{}_q-CH_2CHCH_2R^6$$
$$|$$
$$R^7$$

$$R^5 = -\underset{\underset{CH_2W}{|}}{CH}-CH_2O- \text{ or } -CH_2-\underset{\underset{CH_2W}{|}}{CH}-O-$$

wherein W = halogen.
$R^6$, $R^7$ = one of which is an —OH group the other of which is an —$S_2O_3$Me group,
Me = alkali metal cation or, if necessary, substituted ammonium cation,
n = 3 to 6,
m = 2 to 3,
p = 0 to 100,
q = 0 to 5,
and $R^4 = -(C_xH_{2x})-O-(C_yH_{2y}O)_zR^8$ wherein
$R^8$ = hydrogen, alkyl group with one to four carbon atoms or acetyl group,
x = 3 to 6,
y = 2 to 3,
z = 1 to 100,
with the proviso that in the average molecule at least one $R^2$ group is an $R^3$ group, and, when p=0 in the $R^3$ group, at least One $R^4$ group is present, wherein
a = 1 to 2.33,
b = 0.02 to 1 and
2 ≤ (a+b) ≤ 3.

Advantageously Bunte-salts of the general formula (I), (III), (VI) or (VII) and Keratin-Bunte-salts are used. Bunte-salts of the formula (VI), the formula (III) with P = Adipic acid-Triethylenediamine Polyamide Epichlorohydrin Resin (Hercosett$^R$ 57 or 125 from Hercules Inc./USA) and Keratin-Bunte-Salts are advantageous.

The keratin hydrolysates in the preferred Kerasol$^R$ embodiment which are reacted with sodium thiosulfate to form the keratin Bunte-salts of paragraph number (vi) above are mixtures of soluble keratin proteins which have an average molecular weight of approximately 100,000 Daltons and an amino acid composition comprising 4.9% by weight isoleucine, 10.6% by weight leucine, 5.5% by weight lysine, 1.5% by weight methionine, 2 0% by weight cystine, 3.9% by weight phenylalanine, 4.8% by weight threonine, 1.4% by weight tyrosine, 5.2% by weight valine, 7.6% by weight arginine, 3.8% by weight histidine, 4.2% by weight alanine, 9.1% by weight aspartic acid, 11.4% by weight glutamic acid, 3.3% by weight glycine, 2.4% by weight proline and 8.3% by weight serine.

The Bunte-salts are employed in the shaping agent in an amount of 0.1 to 30 percent by weight, advantageously in the amount of 0.5 to 15 percent by weight.

The pH value of the shaping agent used in the method according to the invention amounts to from 6 to 10, but a pH value under 9, especially a pH value of 6 to 8.5, is preferred.

A swelling and penetrating material, such as dipropyleneglycolmonomethyl ether, urea, 2-pyrrolidone or imidazolidine-2-one, may be added in an amount from about 2 to 30 percent by weight to increase the effectiveness of the shaping agent.

After an acting time sufficient for permanent shaping of hair, which amounts to from 10 to 60 minutes (10 to 30 minutes with heating and 20 to 60 minutes without heating) depending on the application temperature (15° to 80° C.) according to the hair properties, pH value and the shapability of the shaping agent, the hair is rinsed with water and then subjected to an oxidative aftertreatment("fixing"). It is however also possible to perform the oxidative after treatment without prior rinsing with water directly in connection with the shaping process. The agent for oxidative aftertreatment is used according to the hair feel in an amount of from about 80 to 120 grams.

According to additional embodiments of the invention, the hair can be dried prior to the oxidative aftertreatment.

For an oxidative aftertreatment any of the currently used agents for this kind of treatment can be used. For example, alkali metal bromates, such as sodium or potassium bromate, sodium perborate, urea peroxide and hydrogen peroxide, can be used as physiologically acceptable oxidizing agents for the oxidative aftertreatment. The compositions agents used for the oxidative aftertreatment are in the form of an aqueous preparation and contain usually 0.5 to 10 percent by weight of the physiologically acceptable oxidizing agent. Furthermore these compositions can have additional materials, such as weak acids, buffer substances or peroxide stabilizing agents. The acting time of the agents used for the oxidative aftertreatment amounts to about 1 to 20 minutes usually.

Both the shaping agent or means used in the method of the invention and also the means or agent for oxidative aftertreatment can be present in the form of an aqueous solution or an emulsion as well as a concentrated form based on water, especially creams, gels or pastes. Similarly it is also possible to deliver these agents under pressure in aerosol cans and to take a foam from the can. Furthermore the agent for oxidative aftertreatment and also the hair shaping agent can also contain all the standard known cosmetic additives suitable for agents of this type, such as Kaolin, Bentonite, fatty acids, higher fatty alcohols, starch, polyacrylic acid, celluslose derivatives, alginates, petrolatum or paraffin oil; also dyes; turbidity-producing agent, such as polyethylene glycol ester; or alcohols, such as ethanol, propanol, isopropanol or glycerin; solvents; stabilizing agents; buffer substances; perfumes; hair conditioning and/or hair care components, such as lanolin derivatives, cholesterol, pantothenic acid or betain. The mentioned components are used in the usual amounts for that purpose, for example the thickening agents are used in an amount of about 0.1 to 25 percent by weight.

Subsequently the curlers are removed. As the case requires, the curled hair can be oxidatively treated several times. The hair is rinsed with water, as needed set in a permanent wave and subsequently dried.

A physiologically acceptable and uniform natural shaping of the hair from hair roots to the tips of the hair is possible by the previously described process for shaping hair. The hair so shaped has a pleasant touch and a good stability of the curls or permanent wave and is free of an unpleasant odor.

The subject matter is illustrated by the following examples, whose particular details should not be construed as limiting further the claims appended below.

EXAMPLES

Example 1

Method of Permanent Hair Shaping

In connection with a hair wash hand-towel dried hair is wound on curlers with a diameter of 5 millimeters and is moistened with 80 g of hair shaping agent.

| | |
|---|---|
| 6.0 g | Polyamide-Epichlorohydrin-Bunte- Salt of the general formula (III) obtained by reaction of sodium thiosulfate with a polyamide-Epichlorohydrin ("Hercosett$^R$ 125" of Hercules Inc., Wilmington/USA) |
| 2.0 g | Ammonium sulfite |
| 0.2 g | Perfume oil |
| 91.8 g | Water |
| 100. g | (pH adjusted to 10 with sodium hydroxide) |

After an acting time of 30 minutes at 50° C. the hair is rinsed with water and then oxidatively aftertreated with 100 g of an aqueous sodium bromate solution of the following composition("fixing"):

| | |
|---|---|
| 6.0 g | sodium bromate |
| 1.0 g | disodium hydrogen phosphate |
| 0.7 g | sodium dihydrogen phophate |
| 92.3 g | water |
| 100.0 | (pH = 6.2) |

After removing the curlers the hair is rinsed once again with water and subsequently dried.

The hair thus treated has a good shape, which is maintained after many hair washings.

Example 2

Method of Permanent Hair Shaping

Approximately half of the following hair shaping agent is distributed on the hand-towel dried hair, subsequently the hair is wound on curlers with a diameter of about 10 millimeters and then moistened with the remainder of the hair shaping agent.

| | |
|---|---|
| 3.0 g | Keratin- Bunte-Salt, obtained by reaction of sodium thiosulfate with a Keratin hydrolysate ("Kerasol$^R$" from Croda Ltd./Great Britain). |
| 10.0 g | Ammonium hydrogen sulfite |
| 20.0 g | Urea |
| 4.0 g | Ethanol |
| 0.4 g | Cocoalkyldimethyl ammonium betain |
| 0.3 g | Perfume oil |
| 0.2 g | hydrated Ricinus oil, ethoxylated with 45 Mol of ethylene oxide |
| 62.1 g | Water |
| 100. g | (with caustic soda solution at pH 7.0) |

After an acting time of about 20 minutes at 45° C., while the hair is covered with a plastic hood, the hair is rinsed with luke warm water for 3 minutes and then aftertreated oxidatively with 80 gram of a 3% by weight aqueous hydrogen peroxide solution (pH=2.5). Subsequently the curlers are removed, the hair rinsed a new with luke water, set in a permanent wave and then dried.

The hair permanently shaped in this way is easily combinable in a wet and dry state and has a pleasant feel.

Example 3

Method of Permanent Hair Shaping

In connection with a hair washing the hand-towel dried hair is wound on curlers with a diameter of about 8 millimeters and then moistened with the following hair shaping agent.

| | |
|---|---|
| 10.0 g | (3-S-thiosulfato-2-hydroxypropyl)-N,N-dimethylamine of the formula (VI) |
| 6.0 g | sodium sulfite |
| 5.0 g | 2-pyrrolidone |
| 4.0 g | isopropanol |
| 0.4 g | Perfume oil |
| 0.4 g | octyl phenol, ethoxylated with 20 Mol of ethylene oxide |
| 0.2 g | Cocoalkyldimethyl ammonium betain |
| 74.0 g | Water |
| 100.0 g | (with caustic soda solution at pH 8.0) |

The hair is then covered with a plastic hood and heated for twenty minutes at 45° C. Subsequently the hair is rinsed with water and then dried 10 minutes at 50° C.

Then the hair is oxidatively aftertreated as described in Example 1, is set in a permanent wave and dried.

The hair permanently shaped in this way has a high stability, is easily combed and has a pleasant feel.

Example 4

Comparative Tests a) Stability of the Permanent Wave produced Depending on the Oxidative Aftertreatment Two moistened hair strands made from about 100 bleached human hairs were wound on a spiral curler with a diameter of about 5 mm and then saturated with a 0.1 g of one of the following two shaping agents:

| Shaping Agent | (A) | (B) |
|---|---|---|
| Bunte-Salt of the formula (III), obtained by reaction of a Polyamide Epichlorohydrin ("Hercosett$^R$ 125" of Hercules Inc., Wilmington/ USA) with sodium thiosulfate | 6.0 g | 6.0 g |
| Sodium sulfite | 2.0 g | 5.0 g |
| Water | ad 100.0 g | ad 100 g |
| with sodium hydroxide to pH 10 | | |

After acting for 30 minutes at 50° C. both hair strands were rinsed with water and subsequently aftertreated with 0.10 g of an oxidation agent of the following composition:

| 6.0 g | Sodium bromate |
|---|---|
| 1.0 g | disodium hydrogen phosphate |
| 0.7 g | sodium dihydrogen phosphate |
| 92.3 g | water |
| 100. g | (pH = 6.2) |

In a second series of comparison tests, the hair strands were formed in the previously described way, however no oxidative aftertreatment was performed.

Subsequently the hair strands were rinsed with water and dried. Then the stability of the locks so produced ("wave stability") was tested by immersion on the hair strands in water.

The wave stability was determined with the help of the following formula from the measured length of the hair strand after the shaping treatment and the measured length of the hair strand after suspension in water:

Wave stability
[%]={1.0−[(L2−L1)/(L0−L1)×100.

L0=length of the hair strand prior to shaping,
L1=length of the hair strand after shaping and
L2=length of the hair strand after suspension in water.

The larger the value of the wave stability, the more stable is the permanent wave. The results of these comparative experiments are summarized in the following:

TABLE I

| Used Shaping Agent | Oxidative Aftertreatment | Wave Stability, % |
|---|---|---|
| (A) | Yes | 19.2 |
| (A) | No | 16.1 |
| (B) | Yes | 25.4 |
| (B) | No | 13.2 |

The present comparative experiments show that in the method according to the invention a permanent wave is obtained by an oxidative aftertreatment, which has twice the stability of the method described in European Published Patent Application 0 346 151.

b) Stability of the Permanent Wave Produced depending on the pH Value of the Shaping Agent used The hair strands were treated with a hair shaping agent of the following compositions in the manner described under (a) below, the said compositions having a pH-value between 7 and 10:

| Hair Shaping Agent Composition | |
|---|---|
| Bunte- Salt of the formula (III), obtained by reacting a Polyamide Epichlorohydrin ("Hercosett$^R$ of Hercules Inc., Wilmington, USA) with sodium thiosulfate | 10 g |
| Sodium sulfite × 7 H$_2$O | 12.0 g |
| Sodium hydroxide | ad pH 7 to 10 |
| Water | ad 100.0 g |

Subsequently the hair strands were treated oxidatively and dried. For comparison purposes a second hair strand was shaped in the same way, however an oxidative aftertreatment was not used.

The determined wave stability results in the manner described below. The results of this experiment are summarized in Table II:

TABLE II

| pH Value of the Hair Shaping Agent | Wave Stability, % | |
|---|---|---|
| | with oxidative Aftertreatment | without oxidative Aftertreatment |
| 7 | 40.4 | 33.8 |
| 8 | 40.8 | 35.8 |
| 9 | 37.0 | 35.8 |
| 10 | 37.7 | 34.6 |

These comparative experiments clearly show that surprisingly with the method according to the invention with a neutral to mild alkaline shaping agent an improved and more permanent shaping is effected than with strong alkali shaping agent.

While the invention has been illustrated and described as embodied in a method for permanently shaping hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

We claim:

1. In a process for permanent shaping of hair comprising the steps of bringing the hair into a desired shape, treating the hair with a hair shaping agent, rinsing with water, subjecting the hair to an oxidative aftertreatment with an oxidizing agent selected from the group consisting of alkali bromates, sodium perborate, hydrogen peroxide and urea peroxide, setting the hair to form a permanent wave and drying, the improvement wherein the hair shaping agent consists essentially of an aqueous hair shaping composition having a pH from 6 to 8.5, said aqueous hair shaping composition containing 0.1 to 30 percent by weight of at least one Bunte-salt and 0.5 to 30 percent by weight of at least one member selected from the group consisting of sulfites and hydrogen sulfites and wherein said subjecting said hair to an oxidative aftertreatment includes treating said hair with an aqueous oxidative aftertreatment composition containing from 0.5 to 10 percent of said oxidizing agent, and
wherein said a least one Bunte-salt is selected from the group consisting of 2-S-thiosulfatocarboxylic acids of the formula (I):

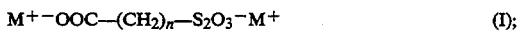

$$M^{+-}OOC-(CH_2)_n-S_2O_3^-M^+ \qquad (I);$$

wherein n is an integer from 1 to 6 and $M^+$ is an alkali metal or ammonium cation;
2-S-thiosulfatoethylamine of the following formula (II):

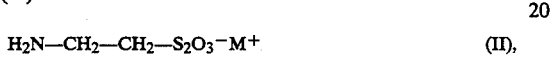

$$H_2N-CH_2-CH_2-S_2O_3^-M^+ \qquad (II),$$

wherein $M^+$ is an alkali metal or ammonium cation;
polyamide-epichlorohydrin-Bunte-salt of the formula (III):

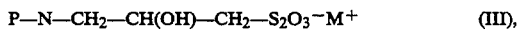

$$P-N-CH_2-CH(OH)-CH_2-S_2O_3^-M^+ \qquad (III),$$

wherein $M^+$ is an alkali metal or ammonium cation and P is a polymer chain;
polyoxyalkylene-Bunte-salts of the formula (IV) or (v):

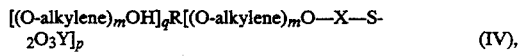

$$[(O\text{-alkylene})_mOH]_qR[(O\text{-alkylene})_mO-X-S_2O_3Y]_p \qquad (IV),$$

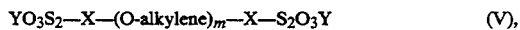

$$YO_3S_2-X-(O\text{-alkylene})_m-X-S_2O_3Y \qquad (V),$$

wherein p=2, 3, 4, 5 or 6;
q=0, 1, 2, 3 or 4;
(p+q)=3, 4, 5 or 6;
m=a whole number <1;
R is a group obtained by cleavage of hydroxyl groups from an aliphatic alcohol having at least two carbon atoms;
X is a divalent substituted or unsubstituted aliphatic group having one to 10 carbon atoms; and
Y is a hydrogen atom, a salt-forming ion or a salt-forming group;
(3-S-thiosulfato-2-hydroxypropyl)-N,N-dimethylamine of the formula (VI):

$$(CH_3)_2N-CH_2-CH(OH)-CH_2-S_2O_3 \qquad (VI);$$

keratin-Bunte salts obtained by reaction of keratin hydrolysates with sodium thiosulfate; and
polysiloxane-Bunte-salts of the formula (VII):

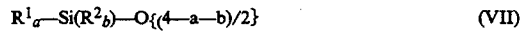

$$R^1{}_a-Si(R^2{}_b)-O_{\{(4-a-b)/2\}} \qquad (VII)$$

wherein from 90 to 100% of the $R^1$ groups are methyl, and from 0 to 10% of the $R^1$ groups are phenyl; and $R^2=R^3$ and/or $R^4$,
wherein
$R^3=-(C_nH_{2n})-O-(C_mH_{2m}O)_p-R^5-q-CH_2CH(R^7)CH_2R^6$
$R_5=-CH(CH_2W)-CH_2O-$ or $-CH_2-CH(CH_2W)-O-$
wherein W=halogen,
$R^6$, $R^7$ include an $-OH$ group and a member selected from the group consisting of $-S_2O_3Me$ wherein Me=a substituted ammonium cation or an alkali metal cation,
n=3 to 6,
m=2 to 3,
p=0 to 100,
q=0 to 5,
and $R^4=-(C_xH_{2x})-O-(C_yH_{2y}O)_zR^8$
wherein $R^8$=hydrogen, an alkyl group with one to four carbon atoms or an acetyl group,
x=3 to 6,
y=2 to 3,
z=1 to 100, with the proviso that at least one $R^2$ group is an $R^3$ group, and, when p=0 in the $R^3$ group, at least one
$R^4$ group is present, wherein a=1 to 2.33,
b=0.02 to 1 and
$2 \leq (a+b) \leq 3$.

2. The improvement as defined in claim 1, wherein said keratin hydrolysates are a mixture of soluble keratin proteins having an average molecular weight of about 100,000 Daltons, said soluble keratin proteins having an amino acid composition comprising 4.9% by weight isoleucine, 10.6% by weight leucine, 5.5% by weight lysine, 1.5% by weight methionine, 2.0% by weight cystsine, 3.9% by weight phenylalanine, 4.8% by weight threonine, 1.4% by weight tyrosine, 5.2% by weight valine, 7.6% by weight arginine, 3.8% by weight histidine, 4.2% by weight alanine, 9.1% by weight aspartic acid, 11.4% by weight glutamic acid, 3.3% by weight glycine, 2.4% by weight proline and 8.3% by weight sering.

3. The improvement as defined in claim 1, wherein the drying is performed prior to the oxidative aftertreatment with the oxidizing agent.

4. The improvement as defined in claim 1, wherein the sulfites are selected from the group consisting of alkali metal sulfites and ammonium sulfites and the hydrogen sulfites are selected from the group consisting of alkali metal hydrogen sulfites, ammonium hydrogen sulfites and alkanolamine salts of sulfurous acid.

5. The improvement as defined in claim 1, wherein the aqueous hair shaping composition is allowed to act on the hair for from 10 to 60 minutes.

6. The improvement as defined in claim 1, wherein in the treating of the hair with the hair shaping agent, the aqueous hair shaping composition is applied to the hair in an amount of from 80 to 120 grams.

7. The improvement as defined in claim 1, wherein said oxidizing agent is allowed to act on the hair during said subjecting for from 1 to 20 minutes.

* * * * *

UNITED STATES PATENT AND TRADEMARK OFFICE
CERTIFICATE OF CORRECTION

PATENT NO. : 5,424,062
DATED : June 13, 1995
INVENTOR(S) : Annette SCHWAN, et al

It is certified that error appears in the above-identified patent and that said Letters Patent is hereby corrected as shown below:

Column 3, Line 23, change "m = a whole number $>$ 1" to --m = a whole number $\geq$ 1".

Column 9, Line 43, change "m = a whole number $>$ 1" to --m = a whole number $\geq$ 1".

Signed and Sealed this

Twenty-fourth Day of October, 1995

Attest:

BRUCE LEHMAN

*Attesting Officer*     *Commissioner of Patents and Trademarks*